United States Patent [19] [11] 4,407,825
Hiestand et al. [45] Oct. 4, 1983

[54] NOVEL BIS- AND POLY-DISULFIDES HAVING IMMUNOSTIMULANT ACTIVITY

[75] Inventors: Peter Hiestand, Allschwil; Michael Strasser, Binningen, both of Switzerland

[73] Assignee: Sandoz Ltd., Basel, Switzerland

[21] Appl. No.: 344,175

[22] Filed: Jan. 29, 1982

[30] Foreign Application Priority Data

Feb. 5, 1981 [GB] United Kingdom ............... 8103513

[51] Int. Cl.$^3$ .................. A61K 31/105; C07C 149/12
[52] U.S. Cl. .................................... 424/336; 424/308; 424/311; 560/112; 560/264; 568/22
[58] Field of Search .................. 568/22; 424/336, 308, 424/311; 560/112, 264

[56] References Cited

U.S. PATENT DOCUMENTS 3,021,215  2/1962  Williams et al. .................... 568/45

FOREIGN PATENT DOCUMENTS 2038836   2/1971  Fed. Rep. of Germany .
2440253   3/1975  Fed. Rep. of Germany .
49-100453 5/1974  Japan .
WO81/01705 6/1981 PCT Int'l Appl. .

OTHER PUBLICATIONS

Click et al., Cellular Immunology 3, 156 (1972).
Broome et al. J. Exp. Medicine 138, 574 (1973).
Makinodan et al., Mech. of Ageing and Dev. 10, 325 (1979).
M. Goodman et al., 4 Immunology 126, (1) 20, (1981).
R. Noelle et al., Cellular Immunology 60, 453 (1981).
E. Assous et al., Therapie, XXVII, 395, 413, 423, 433 (1972).

Primary Examiner—Donald G. Daus
Assistant Examiner—M. C. Eakin
Attorney, Agent, or Firm—Gerald D. Sharkin; Robert S. Honor

[57] ABSTRACT

Compounds of formula

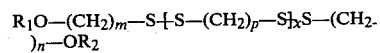

$$R_1O-(CH_2)_m-S-[S-(CH_2)_p-S]_xS-(CH_2)_n-OR_2$$

wherein $R_1$ and $R_2$ are, independently, hydrogen, $C_{1-5}$alkyl or a physiologically-hydrolyzable and -acceptable acid residue; m and n are, independently, 2 or 3; p is an integer of fron 2 to 6; and x is 1, 2 or 3; whereby when x is 2 or 3, each p may be the same or different, having immunostimulant activity.

8 Claims, No Drawings

NOVEL BIS- AND POLY-DISULFIDES HAVING IMMUNOSTIMULANT ACTIVITY

The present invention relates to novel bis- and poly-disulfides having immuno-stimulant activity.

More particularly the present invention relates to bis- and poly-disulfides of formula I,

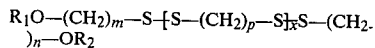
$$R_1O-(CH_2)_m-S-[S-(CH_2)_p-S]_xS-(CH_2)_n-OR_2 \quad (I)$$

wherein $R_1$ and $R_2$ are, independently, hydrogen, $C_{1-5}$alkyl or a physiologically-hydrolysable and -acceptable acid residue, m and n are, independently, 2 or 3, p is an integer of from 2 to 6, and x is 1, 2 or 3, whereby when x is 2 or 3, each p may be the same or different.

Alkyl groups as $R_1$ and $R_2$ may be branched or, preferably, straight-chain. Preferably they contain 1 to 4 carbon atoms, methyl being the most preferred.

By the term "a physiologically-hydrolysable and -acceptable acid residue" is meant an acid residue which is removable by hydrolysis under physiological conditions to yield an acid which is itself physiologically acceptable, e.g. non-toxic, at the dosages administered. Suitable acid residues are, for example, physiologically-hydrolysable and -acceptable acyl residues including carboxylic acyl residues [in particular alkylcarbonyl residues, e.g. ($C_{1-4}$alkyl)-carbonyl residues such as acetyl] and the benzoyl residue.

Preferably $R_1$ and $R_2$ are, independently, hydrogen or $C_{1-5}$alkyl. More preferably $R_1$ and $R_2$ are the same.

m and n are also preferably the same and are most preferably 2.

When x is 2 or 3, each p may be different. Preferably however, each p is the same, and more preferably each p is 2. Most conveniently x is 1.

Especially preferred are compounds of formula I, wherein x is 1 and p is 2.

In one group of compounds in accordance with the invention, $R_1$ and $R_2$ are, independently, hydrogen, $C_{1-5}$alkyl or a physiologically-hydrolysable and -acceptable acyl residue, and x is 1.

The compounds of formula I may be produced in accordance with known methods, e.g. by (a) hydrolysing a compound of formula II,

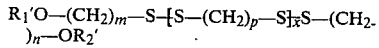
$$R_1'O-(CH_2)_m-S-[S-(CH_2)_p-S]_xS-(CH_2)_n-OR_2' \quad (II)$$

wherein $R_1'$ and $R_2'$ are, independently, hydrogen, $C_{1-5}$alkyl or an acid residue, whereby at least one of $R_1'$ and $R_2'$ is an acid residue, and m, n, p and x have the meanings already given, to produce a compound of formula I, wherein at least one of $R_1$ and $R_2$ is hydrogen;

(b) acylating a compound of formula III,

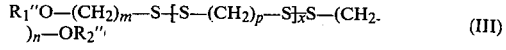
$$R_1''O-(CH_2)_m-S-[S-(CH_2)_p-S]_xS-(CH_2)_n-OR_2'' \quad (III)$$

wherein $R_1''$ and $R_2''$ have the meanings already given for $R_1$ and $R_2$, with the proviso that at least one of $R_1''$ and $R_2''$ is hydrogen, and m, n, p and x have the meanings already given, with an appropriate acid or acid derivative, to produce a compound of formula I, wherein at least one of $R_1$ and $R_2$ is a physiologically-hydrolysable and -acceptable acid residue; or (c) linking together by a dithio bond a first thio compound providing the sequence IV,

$$Z-[S-(CH_2)_p-S]_{x1} \quad (IV)$$

and a second thio compound providing the sequence V,

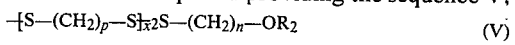
$$-[S-(CH_2)_p-S]_{x2}S-(CH_2)_n-OR_2 \quad (V)$$

whereby $R_1$, $R_2$, m, n and p have the meanings already given, and either (i) Z represents a group of formula $R_1O-(CH_2)_m-S-$, and $x^1$ and $x^2$ are independently zero, 1, 2 or 3, whereby $(x^1+x^2)=1$, 2 or 3, or (ii) Z represents a free valency and $x^1$ is 1 and $x^2$ is zero or 1, or $x^1$ is 2 or 3 and $x^2$ is zero.

Hydrolysis (a) and acylation (b) may be effected in conventional manner, e.g. in the former case in the presence of an appropriate aqueous acid or base, such as HCl or NaOH, and in the latter case by reaction with an appropriate physiologically acceptable acid or reactive derivative thereof. Both reactions are suitably performed in an appropriate aqueous or organic solvent or diluent at a temperature of from, e.g. 0° to 50° C.

Process step (c) may also be conducted in accordance with conventional methods for reaction of thio compounds to complete an —S—S— linkage, e.g. by (c.1) reaction of a compound of formula IVa,

$$Z'-[S-(CH_2)_p-S]_{x1}H \quad (IVa)$$

or a reactive derivative thereof, with a compound of formula Va,

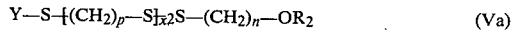
$$Y-S-[(CH_2)_p-S]_{x2}S-(CH_2)_n-OR_2 \quad (Va)$$

whereby $R_1$, $R_2$, m, n and p have the meanings already given, Y is a leaving group, and either (i) Z' represents a group of formula $R_1O(CH_2)_m-S-$, and $x^1$ and $x^2$ are independently zero, 1, 2 and 3, whereby $(x^1+x^2)=1$, 2 or 3, or (ii) Z' represents hydrogen, and $x^1$ is 1 and $x^2$ is zero or 1, or $x^1$ is 2 or 3 and $x^2$ is zero;

(c.2) reaction of a compound of formula IVb,

$$Z''-[S-(CH_2)_p-S]_{x1}Y \quad (IVb)$$

with a compound of formula Vb,

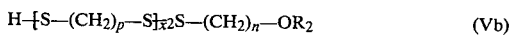
$$H-[S-(CH_2)_p-S]_{x2}S-(CH_2)_n-OR_2 \quad (Vb)$$

or a reactive derivative thereof, whereby $R_1$, $R_2$, m, n, p and Y have the meanings already given, and either (i) Z'' represents a group of formula $R_1O-(CH_2)_m-S-$, and $x^1$ and $x^2$ are independently zero, 1, 2 or 3, whereby $(x^1+x^2)=1$, 2 or 3, or (ii) Z'' represents a leaving group, and $x^1$ is 1 and $x^2$ is zero or 1, or $x^1$ is 2 or 3 and $x^2$ is zero.

(c.3) reaction of a compound of formula IVa with a compound of formula Vb, whereby $Z^1$, $x^1$ and $x^2$ are as defined above and $R_1$, $R_2$, m, n and p have the meanings already given, said reaction being carried out under oxidising conditions.

Reactive derivatives of compounds of formula IVa and Vb above include, for example, the corresponding mono- and bis-alkali metal thiolates, for example the corresponding mono-sodium thiolates of compounds of formula IVa, wherein Z' is $R_1O$—$(CH_2)_m$—S—, or formula Vb, as well as the corresponding bis-sodium thiolates of compounds of formula IVa, whereby Z' is hydrogen. Use of compounds of formula IVa and IVb as such (i.e. not in reactive derivative form) is however preferred.

Suitable leaving groups Z" and Y include, e.g. halogen atoms, in particular chlorine. For formula Va, when $x^2$ is zero, further suitable leaving groups Y are those of formula VI,

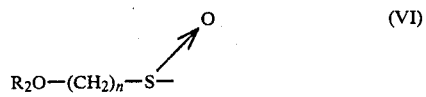

(VI)

wherein $R_2$ and n have the same meaning as the groups $R_2$ and n in formula Va.

Reactions (c.1) and (c.2) are suitably carried out at reduced temperatures, e.g. ca. −60° to −20° C. in an appropriate solvent or diluent. When Z" and Y are leaving groups, e.g. halogen, an aprotic solvent, such as tetrahydrofuran or ethyl acetate is used.

Reaction (c.3) is suitably carried out in the presence of an oxidising agent, such as iodine- or potassium-hexacyanoferrate (III), in the presence of an inorganic base, in particular an alkali metal hydroxide, such as potassium hydroxide. An aqueous or alkanolic, e.g. methanolic, medium may be employed, the reaction conveniently being effected at a temperature of from 0° to 50° C.

It will be appreciated that for processes hereinabove described, wherein Z, Z' or Z" is other than a group of formula $R_1O$—$(CH_2)_m$—S—, the moieties $R_1O$—$(CH_2)_m$—S— and $R_2O$—$(CH_2)_n$—S— of the product compound will be identical.

The starting materials of formula IVa, IVb, Va and Vb are known or may be produced analogously to known compounds. Thus the compound 1,2-ethanedithiol of formula IVa, wherein Z' is hydrogen, $x^1$ is 1 and p is 2, is commercially available. The corresponding 1,2-ethane-bis(sulfenylchloride) of formula IVb, wherein Z" and Y are each chlorine, $x^1$ is 1 and p is 2, is known from the literature and may be produced, e.g. as hereinafter described for Process B of the accompanying Examples.

Compounds of formula Va, wherein $x^2$ is zero and Y is a group of formula VI as defined above, can also be produced, e.g. in accordance with the following reaction scheme.

(1) $R_2O$—$(CH_2)_n$—SH
(VII)→$R_2O$—$(CH_2)_n$—S—S—$(CH_2)_n$—$OR_2$ (VIII)

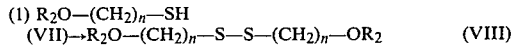

(2) (VIII) $\rightarrow$ 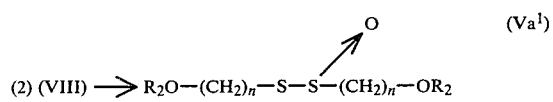

Step (1) above is conveniently performed analogously to oxidisation (c.3) herein above described, step (2) by oxidisation with m-chloroperbenzoic acid in an alkanolic medium at a temperature of from −20° to +30° C.

Compounds of formula Vb, wherein $x^2$ is 1, can also be produced by further reaction of compounds of formula ($Va^1$) above with a compound of formula HS—$(CH_2)_p$—SH, with splitting off of the group

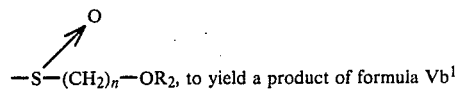, to yield a product of formula $Vb^1$

 ($Vb^1$)

Compounds of formula IVa, wherein Z' is a group of formula $R_1O$—$(CH_2)_m$—S— and $x^1$ is 1, i.e. of formula $IVa^1$,

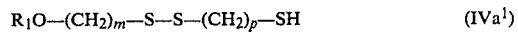 ($IVa^1$)

may be produced analogously to compounds of formula $Vb^1$ above.

Employing intermediates described above and proceeding in accordance with the reaction methods hereinbefore set forth, product compounds of formula I may be obtained, e.g. in which $R_1$ and m, and $R_2$ and n are different, or in which x is 2 or 3, with each p being optionally the same or different.

The following reaction schemes are given by way of example:

(3) 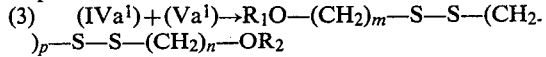

(4) 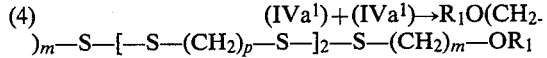

(5) 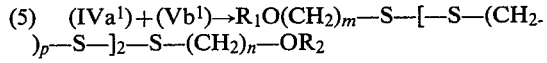

(6) 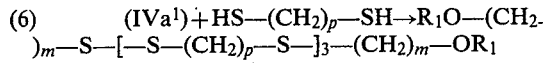

Furthermore, on carrying out processes (c.1) to (c.3) above, using compounds of formula IVa or IVb, wherein $x^1$ is 1 and Z' or Z" is other than $R_1O(CH_2)_m$—S—, product compounds, wherein x is 2 or 3, and $R_1O$—$(CH_2)_m$—S— and $R_3O$—$(CH_2)_n$—S— are the same, are also produced as minor side-products. The relative quantities of these various compounds may readily be increased by appropriate adjustment of the reaction conditions. Obtained compounds of formula I, wherein x is 2 or 3, may be separated from compounds of formula I, wherein x is 1 by conventional techniques, in particular chromatographically.

Compounds of formula II above, not falling within the scope of formula I, may be prepared analogously to process step (c) above.

The following examples are illustrative of the process of the present invention:

EXAMPLE

Preparation of S,S'-ethylene-bis(2-dithioethanol): compound 1

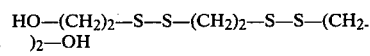

Process A 5 g of ethanedithiol are added with stirring to 41.5 g 2-mercaptoethanol dissolved in 50 ml of water. 200 g potassiumhexacyanoferrate (III) in 500 ml water and 30 g KOH in 200 ml water are then added simultaneously and drop-wise to the obtained colourless, clear solution until the pH reaches 7 to 8.

The addition is terminated when a yellow colouration remains in the reaction medium, and the reaction mixture is then extracted 4x with 100 ml methylene-chloride. The organic phases are combined, dried over magnesium sulphate, filtered and concentrated by evaporation to yield 7.7 g of raw product. This is chromatographed on silica gel using methylene chloride/tetrahydrofuran (4:1) as eluant, to yield the title compound: M.P.=79°–80° C.

Process B 50 g of 1,2-ethane-bis(sulfenylchloride) in 200 ml ethyl-acetate are added to a solution of 59.8 g 2-mercapto-ethanol in 1 liter ethyl-acetate, pre-cooled to −70° C. and under a nitrogen atmosphere. Addition is effected drop-wise with stirring over 15 minutes and in such a way that the temperature does not rise above −65° C. A pale yellow suspension forms, which is poured, immediately on completion of addition of the bis(sulfenylchloride), into 1 liter of water wrmed to 40° C. After vigorous shaking in a separating funnel, the suspension is filtered through hyflo, whereupon two phases are formed. The aqueous phase is extracted twice with 100 ml ethyl-acetate. The combined organic phases are washed with brine, dried over magnesium sulphate, filtered and concentrated by evaporation. The obtained beige oil is chromatographed on silica gel, to yield the title compound: M.P.=77°–80° C.

The 1,2-ethane-bis(sulfenylchloride) used as starting material is produced as follows:

40.5 g of sulfuryl chloride are added drop-wise with stirring at 0° C. to 9.4 g 1,2-ethanedithiol in 50 ml methylene chloride, addition being effected over a period of 20 minutes. A white suspension is formed, which, after prolonged stirring, provides a clear, orange-coloured solution. Stirring is continued for a further 2 hours at 0° C. and the excess sulfuryl chloride and solvent is evaporated off, still at 0° C., using a water-pump vacuum. Residual volatile components are removed from the obtained orange-coloured oil by evaporation for 2 hours under high vacuum. The product 1,2-ethane-bis(sulfenylchloride) is obtained as an orange-coloured solid mass.

The following compounds are recovered as side-products from the initially obtained reaction mixture of Process B above by chromatographic separation, using silica-gel and tetrahydrofuran/methylene chloride (1:4) as eluant.

Compound 2

HO—(CH$_2$)$_2$—S—S—(CH$_2$)$_2$—S—S—(CH$_2$)$_2$—S—S—(CH$_2$)$_2$—OH

M.P.=86°–88° C.

Compound 3

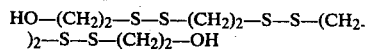
HO—(CH$_2$)$_2$—S—S—(CH$_2$)$_2$—SS—(CH$_2$)$_2$—S—S—(CH$_2$)$_2$—SS—(CH$_2$)$_2$—OH

M.P.=102°–103° C.

The following compound is prepared analogously to process B above, using (2-mercaptoethyl)-methyl ether as starting material in place of 2-mercaptoethanol.

Compound 4

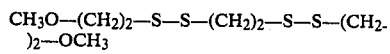
CH$_3$O—(CH$_2$)$_2$—S—S—(CH$_2$)$_2$—S—S—(CH$_2$)$_2$—OCH$_3$ liquid, Rf [thin-layer chromatography on silica-gel with toluene/ethyl acetate (9:1) as carrier medium]=0.36.

In accordance with the present invention it has now surprisingly been found that compounds of formula I are useful as pharmaceutical agents, is particular as immunostimulants.

More particularly it has been found that the said compounds stimulate not only antigen responsive lymphoproliferation, but also anti-body production (primary and secondary immune response) as well as cell-mediated immuno-response. Compounds of formula I are accordingly effective agents for increasing the immune response, in particular the antigenic immune response, of mammals.

The immuno-stimulant activity of the subject compounds may be shown in standard tests both in vitro and in vivo. Thus positive immunostimulant activity is shown for compounds of formula I, e.g. in the following test methods:

IN VITRO

Test I

Mishell/Dutton Test—generation of humoral response by primary immunisation of mouse spleen cells in suspension cultures to heterologous red blood cells [Science 153, 1004 (1966) and J. Exp. Med. 126, 423 (1967)].

Mouse spleen cells are cultured for 3 to 4 days in the presence of antigen (sheep erythrocytes, SE) and test substance. The cells are harvested, washed and plated with fresh antigen (SE) in semi-solid agar. After incubating for 60 minutes, complement is added and incubation continued for a further 90 minutes. Sensitisation of mouse lymphocytes to the antigen during primary culture results in antibody release. In the presence of complement and the secreted specific antibody to SE, the sheep erythrocytes will consequently be lysed (plaque formation). Stimulation of plaque forming cells is observed using compounds of formula I at a concentration of from 0.01 to 10.0 μg/ml.

TEST II

Mixed Lymphocyte Reaction—[Bach et al., J. Exp. Med. 136, 1430 (1972)].

The reaction (i.e. proliferation and differentiation of lymphocytes [mouse (Balb/c) spleen cells] on co-incubation for days, with allogenic spleen cells from irradiated mice (CBA ) is measured in the presence and absence of test-substance. Reaction in the absence of test-substance serves as control and is taken as 100%. Reaction in the presence of test-substance is expressed as the % change compared with the 100% control reaction. Stimulation of reaction is observed using compounds of formula I at a concentration of 0.4 to 10 μg/ml.

TEST III

Secondary Humoral Immunoresponse to the T-cell-specific antigen dinitrophenyl-keyhole limpet hemocyanin (DNP-KLH).

Three weeks after immunisation with DNP-KLH, mice receive a booster injection of the same antigen. The spleens are removed 1 to 4 weeks after "challenge" and a cell culture prepared. The specific anti-bodies developed in response to DNP-KLH antigen, are recovered from the supernatant and measured by ELISA-technique. Test substance is added at varying concentrations during in vitro incubation of the cell culture. Anti-body development in the absence of test substance is used as control and is taken as 100% reaction. Reaction in the present of test-substance is expressed as the % change in reaction compared with the 100% control reaction.

Stimulation of reaction (immuno response) is observed using compounds of formula I at a concentration of 0.4 to 10 µg/ml.

TEST IV

Stimulation of antigen-induced immune interferon production

Lymphocytes [mouse (Balb/c) spleen cells] are co-incubated for 5 days with allogenic spleen cells from irradiated mice (CBA  ) analogously to test II above, in the presence or absence of test substance. The supernatants are collected and tested for levels of immune-interferon (protection of virus infected L929 fibroblasts), units of interferon measured being standardized using a human leucocyte interferon preparation of known potency.

Stimulation of immune interferon production is observed in the above test-method, using compounds of formula I at a concentration of ca. 0.2 to 5.0 µg/ml.

IN VIVO

TEST V

Test for Delayed-Type Hypersensitivity Reaction (cell mediated immunity)—[Dietrich et al., Int. Arch. Allergy 38, 246 (1970)].

Mice are sensitised topically by painting the abdomen with antigen (oxazolone) on day 0. The test compound is administered i.p. or orally on each of the following 5 days. The challenging dose (antigen) is applied on day 9 by painting of the right ear. Skin thickness of both the right and untreated left ear are measured with a microcaliper after a further 24 hours. The mean difference in ear thickness between the two ears is taken as the parameter for evaluating the reaction. Pronounced stimulation of delayed-type hypersensitivity reaction is observed in healthy, mature mice having a normal immune response on administration of compounds of formula I at a dosage of from 0.1 to 10 mg/kg daily for 5 days i.p. or orally.

TEST VI

Jerne Test—generation of humoral responses (assay for haemolytic plaque forming cells)—[Jerne et al., "Cell Bound Antibodies" (ed. Amos and Koprowski), Wistar Inst. Press., Philadelphia, U.S.A. pp. 109–1221].

Mice are sensitised by i.v. injection of sheep erythrocytes (SE) and the test substance administered i.p. on day 0. After 4 to 10 days the mice are sacrificed and a spleen cell suspension prepared. The cell suspension is plated, together with fresh antigen (SE), on semi-solid agar and incubated for 2.5 hrs. in the presence of complement. Sensitised lymphocytes secrete anti-body in response to antigen and, in the presence of complement, the antigen (SE) is lysed (plaque formation).

Administration of compounds of formula I at a dosage of from 0.1 to 1.0 mg/kg results in an increase both of 1 gM as well as 1 gG antibodies.

TEST VII

Activation of natural killer cells

Test substance is administered i.p. or p.o. to nude (athymic) mice (Balb/c or C57/BL). After 16 hours the spleens are removed and the spleen cells incubated for 4 hrs. with chromium labelled target cells (YAK-1). Natural killer cells destroy the target cells, releasing labelled chromium into the supernatant. The supernatant is collected and the amount of chromium released measured by means of a scintillation counter. Release from target cells incubated with spleen cells from untreated mice is used as control and is taken as 100% and release following administration of test substance expressed as the % change in release compared with the control.

Increase in chromium release is observed subsequent to administration of compounds of formula I at dosages of from 0.1 to 10.0 mg/kg.

The compounds of formula I are accordingly useful as immuno-stimulants, e.g. as immunological adjuvants, as systemic immuno-potentiators and as stimulators of non-specific host resistance. Compounds of formula I are thus suitable for e.g. the treatment or supportive treatment (i.e. in combination with other specific or supportive therapy) of conditions associated with impaired immune response, especially impaired humoral response and/or delayed-type hypersensitivity and of condititons where elevation of the immune response is otherwise indicated. In particular, the compounds of formula I are useful for the treatment of supportive treatment of morbid conditions arising from idiopathic immune deficiencies or as occurring in geriatric patients and patients with sever burns or general infections. The compounds of formula I are also indicated for the treatment of supportive treatment of viral illnesses (such as disseminated herpes, progressive vaccinia and disseminated varicella) as well as of Hodgkins Disease and other malignant tumors.

For the above use the dosage will, of course, vary depending upon the compound employed, the mode of administration and therapy desired. However, in general, satisfactory results are obtained when administered at a dosage of from about 10 µg/kg to 10 mg/kg once for adjuvant effect, e.g. in supportive treatment, or daily. For daily administration the compound is conveniently given in divided doses 2 to 4 times a day or in sustained release form. For the larger mammals the total single or daily dosage is in the range of from about 0.1 mg to about 70 mg and dosage forms suitable for oral administration comprise from about 0.025 mg to about 35 mg or, in the case of single dosages, up to 70 mg of active ingredient admixed with a solid or liquid pharmaceutical carrier.

Having regard to their utility as immuno-stimulants, compounds of formula I are also useful as adjuvants for vaccines. For such use satisfactory results are obtained at a dose of from about 0.01 mg to about 1.0 mg/kg on the day of vaccination, with an optional follow-up application at the same dosage 2 to 4 weeks later. For larger mammals a suitable dosage form for oral administration as a vaccine adjuvant comprises from about 0.5 mg to about 100 mg or, preferably, about 70 mg active ingredient.

As already noted, a suitable daily dosage for any particular compound of formula I will depend, inter al., on its relative potency of activity. Potency for the preferred compound in accordance with the invention, namely ethylene-2,2'-bis-(dithiol)bis(ethanol) (compound A), is indicated in the following table, where obtained results for tests II and III above are compared with results for the compound Levamisol (compound B), which is used clinically as an experimental immunostimulant.

|  | Concentration $\mu g/ml^{-1}$ | % change compared with 100% for untreated controls | |
| --- | --- | --- | --- |
|  |  | COMPOUND A | COMPOUND B |
| TEST II | 10.0 | +403% | +45% |
|  | 2.0 | +777% | +13% |
|  | 0.4 | +133% | +13% |
| TEST III | 10.0 | +317% | +16% |
|  | 2.0 | +297% | +2% |
|  | 0.4 | +264% | −27% |

Pharmaceutical compositions comprising the compounds of formula I may be prepared in accordance with standard galenical techniques, e.g. by admixture with conventional pharmaceutically acceptable diluents, carriers or other excipients. Such formulations are conveniently compounded, e.g. in tablet or capsule form or in forms suitable for injection.

In accordance with the foregoing the present invention also provides a compound of formula I as hereinbefore defined for use as a pharmaceutical (i.e. for use in a method of treatment or therapy), in particular for use as an immunostimulant, especially for use in treatment or supportive treatment, e.g. of conditions associated with impaired immune response as hereinbefore set forth.

In a further aspect the invention also provides a method of stimulating the immune response of a subject in need of such treatment which method comprises administering an effective amount of a compound of formula I as hereinbefore defined.

In a yet further aspect the invention also provides a pharmaceutical composition comprising a compound of formula I as hereinbefore defined, together with a pharmaceutically acceptable diluent or carrier therefor.

We claim:

1. A compound of formula I

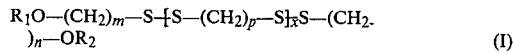

wherein
$R_1$ and $R_2$ are, independently, hydrogen, $C_{1-5}$ alkyl or a non-toxic acid residue which is removable by hydrolysis under physiological conditions,
m and n are, independently, 2 or 3,
p is an integer of from 2 to 6 and
x is 1, 2 or 3,
whereby, when x is 2 or 3, each p may be the same or different.

2. A compound according to claim 1 of formula I, wherein x is 1.

3. A compound according to claim 1 of formula

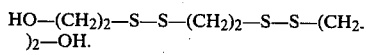

4. A compound according to claim 1 of formula

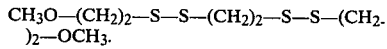

5. A compound according to claim 1 of formula

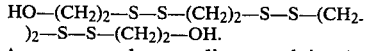

6. A compound according to claim 1 of formula

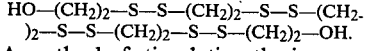

7. A method of stimulating the immune response of a mammal in need of such treatment, which method comprises administering to said subject an amount of a compound of formula I as defined in claim 1 sufficient to effect immunostimulation.

8. An immuno-stimulant composition comprising an immuno-stimulant effective amount of a compound of formula I as defined in claim 1 together with a pharmaceutically acceptable diluent or carrier therefor.

* * * * *